(12) United States Patent
Simons et al.

(10) Patent No.: US 7,202,217 B1
(45) Date of Patent: *Apr. 10, 2007

(54) METHOD FOR PR-39 PEPTIDE REGULATED STIMULATION OF ANGIOGENESIS

(75) Inventors: Michael Simons, Chestnut Hill, MA (US); Youhe Gao, Brighton, MA (US)

(73) Assignee: Beth Israel Deacones Medical Center, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/276,868

(22) Filed: Mar. 26, 1999

Related U.S. Application Data

(60) Provisional application No. 60/103,966, filed on Oct. 13, 1998.

(51) Int. Cl.
*A61K 38/00* (2006.01)

(52) U.S. Cl. .............................. 514/16; 514/12; 514/14; 514/15; 530/300; 530/324; 435/4

(58) Field of Classification Search ................. 514/12, 514/14, 15, 16; 530/324, 300; 435/4
See application file for complete search history.

(56) References Cited

U.S. PATENT DOCUMENTS 5,654,273 A * 8/1997 Gallo et al. ................... 514/12
5,830,993 A * 11/1998 Blecha ........................ 530/300
6,133,233 A   10/2000 Ross et al. .................... 514/12
2004/0009463 A1* 1/2004 Simons et al. ................ 435/2

FOREIGN PATENT DOCUMENTS

WO    WO-9632129    * 10/1996

OTHER PUBLICATIONS

The Washington Post "Should You Be Checked for Diabetes" by Dianne Holes, pp. 4-6, Feb. 4, 2001.*
Feit et al. "Inherency in Patent Law." J. Pat. Trade Off. Soc. vol. 85, No. 1, pp. 5-21 (2003).*
Chan et al. , J. Biol. Chem. 273, 28978-28985 (Oct. 1998).*
Gerads et al., *Cell Mol. Life Sci. 54*:253-262 (1998).
Gerads et al., *J. Mol. Biol. 275*:113-121 (1998).
Baumeister et al., *Cell 92*:367-380 (1998).

* cited by examiner

*Primary Examiner*—Chih-Min Kam
(74) *Attorney, Agent, or Firm*—Licata & Tyrrell P.C.

(57) ABSTRACT

The present invention provides both a method and means for regulating angiogenesis within living cells, tissues, and organs in-situ. The regulation is performed using native PR-39 peptide or one of its shorter-length homologs, for direct interaction with the $\alpha 7$ subunit of such proteasomes as one present in the cytoplasm of viable cells. The result of PR-39 peptide interaction with proteasomes is a decrease in the intracellular degradation of active peptides such as HIF-1$\alpha$ and a consequential stimulation of angiogenesis in-situ.

1 Claim, 9 Drawing Sheets

```
Mouse  MSSIGTGYDL  SASTFSPDGR  VFQVEYAMKA  VENSSTAIGI  RCKDGVVFGV
Human  ----------  ----------  ----------  ----------  ----------

EKLVLSKLYE  EGSNKRLFNV  DRHVGMAVAG  LLADARSLAD  IAREEASNFR
       ----------  ----------  ----------  ----------  ----------

SNFGYNIPLK  HLADRVAMYV  HAYTLYSAVR  PFGCSFMLGS  YSANDGAQLY
       ----------  ----------  ----------  ----------  --V-------

MIDMSGVSYG  YWGCAIGKAR  QAAKTEIEKL  QMKEMTCRDV  VKEVAKIIYI
       ----------  ----------  ----------  ---------I  ----------

VHDEVKDKAF  ELELSWVGEL  TKGRHEIVPK  DIREEAEKYA  KESLKEEDES
       ----------  ----------  -N--------  -I--------  ----------

DDDNM (SEQ ID NO:7)
       -----
```

FIG. 1A

```
        C-TERMINAL TAILS                                NET CHARGE
α1  AERD (SEQ ID NO:8)                                      -1
α2  A                                                        0
α3  KKHEEEEAKAEREKKEKEQKEKDK (SEQ ID NO:9)                  +1
α4  EKEKEENEKKKQKKAS (SEQ ID NO:10)                         +2
α5                                                           0
α6  EERPQRKAQPAQPADEPAEKADEPMEH (SEQ ID NO:11)              -3
α7  AKESLKEEDESDDDNM (SEQ ID NO:12)                         -6
```

FIG. 1B

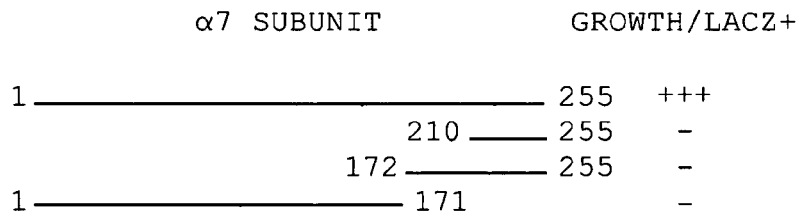

FIG. 1C

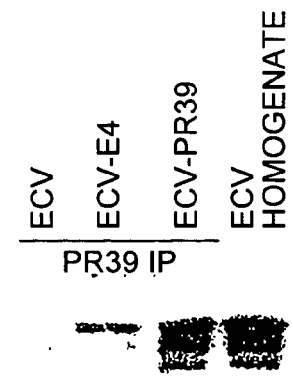

FIG. 1D

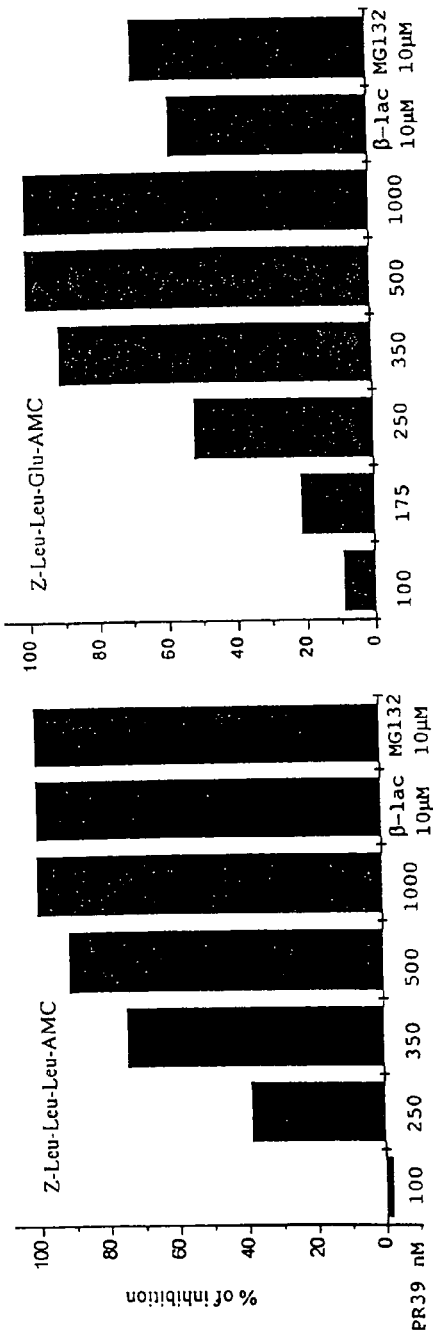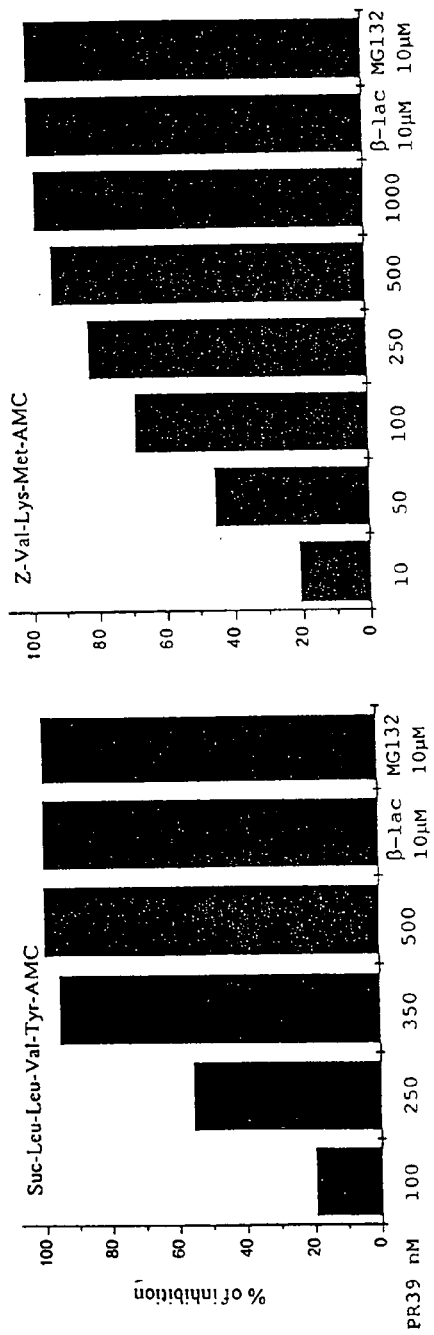

Control
PR 39

* P=0.019

Flow Scheme A

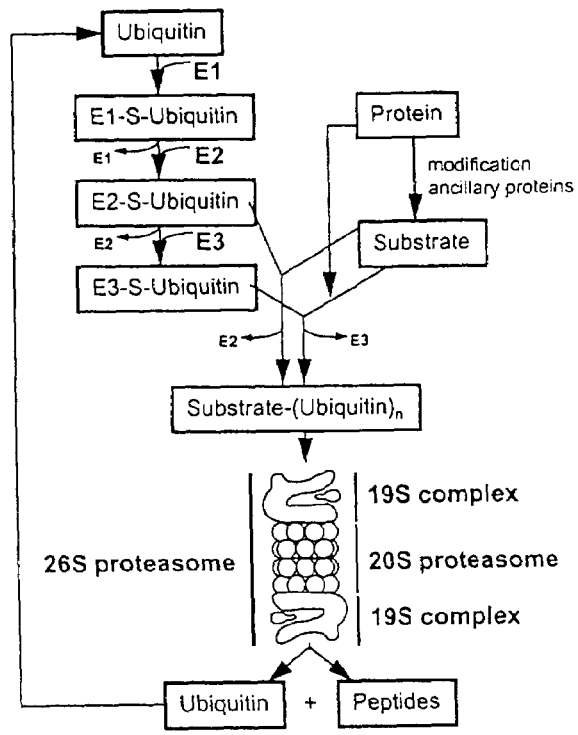

\*
Schematic representation of the proteasome–ubiquitin pathway. Ubiquitin is first activated by a ubiquitin-activating enzyme (UBA or E1) and passed on to a ubiquitin-conjugating protein (UBC or E2). Ubiquitin is then linked directly, or with the help of ubiquitin ligases (E3), via an isopeptide bond to a lysine residue of the substrate protein. Polyubiquitinated proteins are recognized and selectively degraded by the 26S proteasome, yielding reusable ubiquitin molecules and peptides of 5 to 15 amino acids. Conversion of a protein into a substrate for ubiquitination can in certain cases occur after posttranslational modification or association with ancillary factors. Proteins can also be recognized by an E3 ubiquitin ligase without prior modification or association

---

\* Reproduced from Gerards et al., CMLS 54: 253-262 (1998)

Fig. 8

Table 3: Schematic representation of the human 20S proteasome*

* Reproduced from Gerards et al., CMLS 54: 253-262 (1998)

(1) GENERAL INFORMATION:
    (i) APPLICANT:  Children's Medical Center Corporation
    (ii) TITLE OF INVENTION: Synducin Mediated Modulation of Tissue Repair
    (iii) NUMBER OF SEQUENCES:  4
    (iv) CORRESPONDENCE ADDRESS:
        (A) ADDRESSEE:  Patrea L. Pabst
        (B) STREET: 2800 One Atlantic Center
                    1201 West Peachtree
        (C) CITY: Atlanta
        (D) STATE: Georgia
        (E) COUNTRY: USA
        (F) ZIP: 30309-3450
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (ix) TELECOMMUNICATION INFORMATION:
        (A) TELEPHONE: (404) 873-8794
        (B) TELEFAX: (404) 815-8795
(2) INFORMATION FOR SEQ ID NO:1:
    (i) SEQUENCE CHARACTERISTICS:
        (A) LENGTH: 39 amino acids
        (B) TYPE: amino acid
        (D) TOPOLOGY: linear
    (ii) MOLECULE TYPE: peptide
    (iii) HYPOTHETICAL: NO
    (iv) ANTI-SENSE: NO
    (X) PUBLICATION INFORMATION:
        (A) AUTHORS: Lee, Jong-Youn
                     Boman, Hans G.
                     Mutt, Viktor
                     Jornvall, Hans
        (B) TITLE: Novel Polypeptides And Their Use
        (C) JOURNAL: PCT WO 92/22578
        (G) DATE: 12/23/92
        (K) RELEVANT RESIDUES IN SEQ ID NO:1 FROM 1 TO 39
    (xi) SEQUENCE DESCRIPTION: SEQ ID NO:1:

Arg Arg Arg Pro Arg Pro Pro Tyr Leu Pro Arg Pro Arg Pro Pro Pro
1               5                   10                  15
Phe Phe Pro Pro Arg Leu Pro Pro Arg Ile Pro Pro Gly Phe Pro Pro
            20                  25                  30
Arg Phe Pro Pro Arg Phe Pro (SEQ ID NO:1)
        35

FIG. 10

METHOD FOR PR-39 PEPTIDE REGULATED STIMULATION OF ANGIOGENESIS

PROVISIONAL PATENT APPLICATION

The subject matter as a whole comprising the present invention was first filed with the U.S. Patent and Trademark Office as Provisional Patent Application No. 60/103,966 on Oct. 13, 1998.

RESEARCH SUPPORT

The research effort for the invention was supported in part by grants from the National Institutes of Health, grants RO1 HL 53793 and P50 HL 56993 (MS), F32 HL 10013 (RV); and by a grant from Chiron Corporation.

FIELD OF THE INVENTION

The present invention is concerned generally with the induction of angiogenesis within viable cells comprising living tissues and organs; and is particularly directed to mechanisms regulated by PR-39 peptides which result in a stimulation of angiogenesis on-demand and may be used as a controlled therapeutic treatment.

BACKGROUND OF THE INVENTION

Angiogenesis, by definition, is the formation of new capillaries and blood vessels within living tissues; and is a complex process first recognized in studies of wound healing and then within investigations of experimental tumors. Angiogenesis is thus a dynamic process which involves extracellular matrix remodeling, endothelial cell migration and proliferation, and functional maturation of endothelial cells into mature blood vessels [Brier, G. and K. Alitalo, *Trends Cell Biology* 6: 454–456 (1996)]. Clearly, in normal living subjects, the process of angiogenesis is a normal host response to injury; and as such, is an integral part of the host body's homeostatic mechanisms.

It will be noted and appreciated, however, that whereas angiogenesis represents an important component part of tissue response to ischemia, or tissue wounding, or tumor-initiated neovascularization, relatively little new blood vessel formation or growth takes place in most living tissues and organs of mature adults (such as the myocardium of the living heart) [Folkman, J. and Y. Shing, *J. Biol. Chem.* 267: 10931–10934 (1992); Folkman, J., *Nat. Med.* 1: 27–31 (1995); Ware, J. A. and M. Simons, *Nature Med.* 3: 158–164 (1997)]. Moreover, although regulation of an angiogenic response in-vivo is a critical part of normal and pathological homeostasis, relatively little is presently known about the control mechanisms for this process.

Overall, a number of different proteins, growth factors and growth factor receptors have been found to be involved in the process of stimulation and maintenance of angiogenic responses. For example, a number of cell membrane-associated proteins are thought to be involved in the processes of angiogenesis. Such proteins include SPARC [Sage et al., *J. Cell Biol.* 109: 341–356 (1989); Motamed K. and E. H. Sage, *Kidney Int.* 51: 1383–1387 (1997)]; thrombospondin 1 and 2 respectively [Folkman, J., *Nat. Med.* 1: 27–31 (1995); Kyriakides et al., *J. Cell Biol.* 140: 419–430 (1998)]; and integrins $\alpha v \beta 5$ and $\alpha v \beta 3$ [Brooks et al., *Science* 264: 569–571 (1994); Friedlander et al., *Science* 270: 1500–1502 (1995)]. In addition, a major role is played by heparin-binding growth factors such as basic fibroblast growth factor (bFGF) and vascular endothelial growth factor (VEGF); and thus the regulation of angiogenesis is believed today to involve matrix components such as extracellular heparin sulfate and core proteins such as syndecans which are found at the surface of endothelial cells.

However, while a number of heparin binding growth factors (including VEGF, FGF1 and FGF2) have been shown to promote angiogenesis in-vitro and in-vivo, their process involvement appears limited to tissues demonstrating some form of inflammatory response to trauma (as defined by the presence of blood-derived macrophages), be it a direct tissue injury (such as wounding) or ischemia. Moreover, the presence of blood-derived macrophages is also routinely associated with localized secretion of a number of proteins including cytokines such as IL-2 and TNF-$\alpha$, growth factors such as VEGF and FGF-2, matrix metalloproteinases as well as many other biologically active molecules. Accordingly, although there have been many investigations, publications, and developments of these entities, there remains a general ignorance and failure of understanding by research investigators and clinicians alike regarding useful and effective specific means and methods for inducing angiogenesis on-demand within living cells, tissues, and organs. Thus, while the value and desirability of initiating new vascularization—especially using cells in localized areas on an as needed basis as well as a therapeutic treatment for individual patients—is well recognized, these aims remain a long sought goal yet to be achieved in a practical manner.

SUMMARY OF THE INVENTION

The present invention has multiple aspects and uses. A first aspect provides a method for stimulating angiogenesis within a targeted collection of viable cells in-situ, said method comprising the steps of:

identifying a collection of cells comprising viable cells in-situ as a target for stimulation of angiogenesis;

providing means for effecting an introduction of at least one member selected from the group consisting of the PR-39 oligopeptide collective to the cytoplasm of said targeted collection of cells;

introducing at least one member of the PR-39 oligopeptide collective to the cytoplasm of said targeted collection of cells using said effecting means;

allowing said introduced PR-39 oligopeptide collective member to interact with such proteasomes as are present within the cytoplasm of said targeted collection of cells whereby (a) at least the $\alpha 7$ subunit of the proteasomes interacts with said PR-39 oligopeptide collective member, and (b) at least a part of the proteolytic activity mediated by proteasomes with an interacting $\alpha 7$ subunit becomes selectively altered, and (c) the selectively altered proteolytic activity of the proteasomes with an interacting $\alpha 7$ subunit results in a stimulation of angiogenesis in-situ within the targeted collection of viable cells.

A second aspect of the invention provides a method for selective inhibition of proteasome-mediated degradation of peptides in-situ within a collection of viable cells, said method comprising the steps of:

identifying a collection of cells comprising viable cells in-situ as a target;

providing means for effecting an introduction of at least one member selected from the group consisting of the PR-39 oligopeptide collective to the cytoplasm of said targeted collection of cells;

introducing at least one member of the PR-39 oligopeptide collective to the cytoplasm of said targeted collection of cells using said effecting means;

allowing said introduced PR-39 oligopeptide collective member to interact with such proteasomes as are present within the cytoplasm of said targeted collection of cells whereby (a) at least the α7 subunit of the proteasomes interacts with the PR-39 oligopeptide collective member, and (b) at least a part of the proteolytic activity mediated by proteasomes with an interacting α7 subunit becomes markedly altered, and (c) the markedly altered proteolytic activity of the proteasomes with an interacting α7 subunit results in a selective inhibition of proteasome-mediated degradation of peptides in-situ within the targeted collection of cells.

BRIEF DESCRIPTION OF THE FIGURES

The present invention may be more fully understood and better appreciated when taken in conjunction with the accompanying drawing, in which FIGS. 1A–1D are presentations of empirical data showing the direct interaction between PR-39 peptide and the α7 subunit of proteasomes intracellularly, wherein FIG. 1A recites the amino acid sequence of cloned mouse α7 subunit (SEQ ID NO:7) and FIG. 1B shows the sequence alignment of C-terminal tails of mouse α subunits α1 (SEQ ID NO:8), α2, α3 (SEQ ID NO:9), α4 (SEQ ID NO:10), α5, α6 (SEQ ID NO:11), and α7 (SEQ ID NO:12);

FIGS. 3A–3D are graphs demonstrating the results of in-vitro proteasome activity assays;

FIG. 8 presents Flow Scheme A illustrating a schematic representation of the proteasome-ubiquitin pathway;

FIG. 10 presents Table 4 [SEQ ID No:1] which provides background information about the PR-39 peptide.

DETAILED DESCRIPTION OF THE INVENTION

Figure 2C:
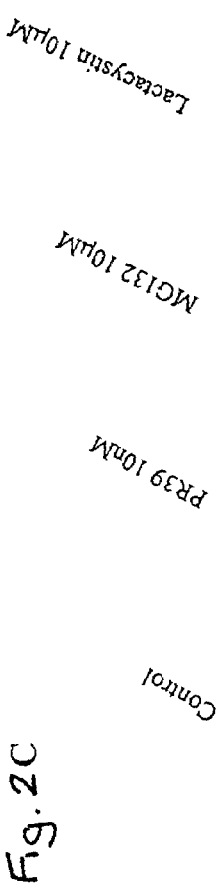
FIGS. 2A–2D are presentations of empirical data showing the effect of PR-39 peptide upon proteasome activity in-vivo.

The present invention is a method for stimulating angiogenesis via the purposeful introduction of native PR-39 peptide or a member of the PR-39 derived oligopeptide family to the cytoplasm of viable cells in-situ. The PR-39 peptide or the derived member of the family will interact with the α7 subunit of such proteasomes as are present intracellularly; and the consequence of PR-39 peptide/proteasome interaction is the selective inactivation of proteasomes such that intracellular degradation of proteins such as HIF-1α and IκBα is diminished and a marked stimulation of angiogenesis in-situ consequently results.

A number of major benefits and advantages are therefore provided by the means and methods comprising the present invention. These include the following:

1. The present invention provides an in-situ stimulation of angiogenesis. By definition, therefore, both in-vivo and in-vitro circumstances of use and application are envisioned and expected. Moreover, the viable cells which are the location of PR-39 peptide and proteasome interaction, alternatively may be isolated cells; be part of living tissues comprising a variety of different cells such as endothelial cells, fibrocytes and muscle cells; and may also comprise part of specific organs in the body of a living human or animal subject. While the user shall choose the specific conditions and circumstances for practicing the present invention, the intended scope of application and the envisioned utility of the means and methods described herein apply broadly to living cells, living tissues, functional organs and systems, as well as the complete living body unit as a viable whole.

2. The present invention has a variety of different applications and uses. Of clinical and medical interest and value, the present invention provides the opportunity to stimulate angiogenesis in tissues and organs in a living subject which has suffered defects or has undergone anoxia or infarction. A common clinical instance is the myocardial infarction or chronic myocardial ischemia of heart tissue in various zones or areas of a living human subject. The present invention thus provides opportunity and means for specific site stimulation and inducement of angiogenesis under controlled conditions. The present invention also has major research value for research investigators in furthering the quality and quantity of knowledge regarding the mechanisms controlling angiogenesis under a variety of different conditions and circumstances.

3. The present invention envisions and permits a diverse range of means for introducing native PR-39 peptide or a shorter-length peptide of the oligopeptide family to a specific location, site, tissue, organ, or system in the living body. A variety of different routes of administration are available to the practitioner; and a wide and useful choice of delivery systems are conventionally available, and in accordance with good medical practice are adaptable directly for use. In this manner, not only are the means for PR-39 peptide introduction under the control of the user, but also the manner of localized application and the mode of limiting the area of peptide introduction can be chosen and controlled.

I. Underlying Mechanism for Initiating s Stimulation of Angiogenesis

The present invention utilizes and relies upon a novel and previously unknown mechanism of interaction between PR-39 peptide (or its shorter-length homologs) and the α7 subunit of proteasomes in-situ as the basis for stimulation of angiogenesis in cells, living tissues, and organs. Evidence of such direct intracellular interaction is provided by the experiments and empirical data described hereinafter. Such direct interactions between proteasomes (and its α7 subunit in particular) and PR-39 peptides collectively are previously unknown; in fact, no meaningful relationship or interaction between any peptide whatsoever and intracellular proteasome function has ever been proposed or envisioned before the present invention was conceived or demonstrated empirically.

As shown experimentally hereinafter, the PR-39 peptide (and the shorter-length PR-39 derived oligopeptide family members) when introduced into the cytoplasm of viable cells will interact and bind with the α7 subunit of 20S proteasomes. The interaction between the collective of PR-39 oligopeptides and the proteasome (α7 subunit is direct; no intermediaries or cofactors are involved in the binding reaction; and such direct binding interactions result in a selective inactivation and inhibition of proteasome function intracellularly such that expression of proteins such as HIF-1α is increased and stimulation of angiogenesis subsequently occurs.

To obtain a direct binding and proteasome interaction in-situ, the introduction of native PR-39 peptides (or its substituted forms, or its shorter-length homologs) is a necessary prerequisite; and the presence of sufficient PR-39 peptide (or its equivalent) quantitatively to bind to the α7 subunit and selectively inactivate proteasomes intracellularly within viable cells can be achieved under both in-vivo conditions and in-vitro experimental circumstances.

The methodology and means provided by the present invention for selectively inhibiting proteolysis and stimulating angiogenesis within viable cells is therefore directed at and focused upon the intracellular degradation capability and functional activity of proteasomes. Such selective inhibition and/or disruption of proteasome-mediated degradation is achieved via the introduction of native PR-39 peptide or a member of the shorter-length PR-39 derived oligopeptide family in a therapeutic regimen of treatment.

II. Proteasomes

The proteasome is a component of the ubiquitin-proteasome-dependent proteolysis system. This system plays a major role in the turnover of intracellular proteins, of misfolded proteins, and in the selective degradation of key proteins. Controlled protein degradation is an important and efficient way to remove nonfunctional proteins and/or to regulate the activity of key proteins. Target proteins are selectively recognized by the ubiquitin system and subsequently marked by covalent linkage of multiple molecules of ubiquitin, a small conserved protein. The polyubiquitinated proteins are degraded by 26S proteasome. This complex, however, is composed of two large subcomplexes: the 20S proteasome constituting the proteolytic core and the 19S regulatory complex which confers polyubiquitin binding and energy dependence. A simplified scheme of the ubiquitin pathway is depicted by Flow Scheme A presented by FIG. 8 hereinafter.

A substantial quantum of research has been conducted to understand the architecture, assembly, and molecular biology of the proteasome. Merely representative of scientific publications in this field are the following, the individual texts of which are expressly incorporated by reference herein: Goldberg et al., *Biol. Chem.* 378: 131–140 (1997); Tanaka, K., *Biochem. Biophys. Res. Commun.* 247: 537–541 (1998); Baumeister et al., *Cell* 92: 367–380 (1998); Gerards et al., *CMLS* 54: 253–262 (1998); Maurizi, M. R., *Curr. Biol.* 8: R453–R456 (1998); Rechsteiner et al., *J. Biol. Chem.* 268: 6065–6068 (1993); Gerards et al., *J. Mol. Biol.* 275: 113–121 (1998); Fenteany, G. and S. Schreiber, *J. Biol. Chem.* 273: 8545–8548 (1998); and Oikawa et al., *Biochem. Biophys. Res. Commun.* 246: 243–248 (1998).

The 20S Proteasome

The degrading component in ubiquitin-dependent protealysis is the 26S proteasome. The catalytic core of this complex is the 20S proteasome, which is highly conserved and can be found in eukaryotes, archaebacteria, and some eubacteria. In eukaryotes, the amount of proteasomes can constitute up to 1% of the cell content, depending on the average protein breakdown rates of the organ. Proteasomes are localized in the nucleus and the cytosol, sometimes colocalizing or associating with the cytosketon. [See for example: Hilt, W. and D. H. Wolf, *Trends Biochem. Sci.* 21: 96–102 (1996); Ciechanover, A., *Cell* 79: 13–21 (1994); Jentseh, S. and S. Schlenker, *Cell* 82: 881–884 (1995); Coux et al., *Annu. Rev. Biochem.* 65: 807–847 (1996); Dahlmann et al., *FEBS Lett.* 251: 125–131 (1989); Tamura et al., *Curr. Biol.* 5: 766–774 (1995); Machiels et al., *Eur. J. Cell Biol.* 66: 282–292 (1995); Scherrer, K. and F. Bey, *Prog. Nucleic Acid Res. Mol. Biol.* 49: 1–64 (1994); and Gerards et al., *CMLS* 54: 253–262 (1998)].

The first description of a "cylinder-shaped" complex with proteasome-like features dates back to the late 1960s. The plethora of names given to it subsequently is a reflection of the problems that were encountered over a period of two decades in trying to define its biochemical properties and cellular functions. Enzymological studies revealed an array of distinct proteolytic activities and led to a consensus name, 'multicatalytic proteinase'. This name, however, was soon replaced by a new one, the 'proteasome' emphasizing its character as a molecular machine.

At about the same time, it was found that the occurrence of proteasomes was not restricted to eukaryotic cells. A compositionally simpler, but structurally strikingly similar proteolytic complex was found in the archaeon *Thermoplasma acidophilum*, which later took a pivotal role in elucidating the structure and enzymatic mechanism of the proteasome.

Nomenclature

The 20S proteasome was independently discovered by groups working in different fields, and hence was given a variety of different names. In 1970, Scherrer and colleagues observed ring-shaped particles in ribosome-free messenger RNA (mRNA) preparations [Sporh et al., *Eur. J. Biochem.* 17: 296–318 (1970)]. Subsequently, in 1979, DeMartino and Goldberg isolated a 700-kDa 'neutral protease' from rat liver [DeMartino, G. N. and A. L. Goldberg, *J. Biol. Chem.* 254: 3712–3715 (1997)]. Then, in 1980 Wilk and Orlowski isolated a large protease complex from the pituitary that possessed three different catalytic activities. They called it multicatalytic protease [Wilk, S. and M. Orlowski, *J. Neurochem.* 35: 1172–1182 (1980); Wilk, S. and M. Orlowski, *J. Neurochem.* 40: 842–849 (1983)]. Later, Monaco and McDevitt immunoprecipitated complexes consisting of low molecular weight proteins (LMPs) with a possible role in antigen presentation [Monaco, J. J. and H. O. McDevitt, *Nature* 309: 797–799 (1984)]. Also, in 1984 this particle was called prosome, referring to its presumed role in programming mRNA translation [Schmid et al., *EMBO* 3: 29–34 (1984)]. Altogether, this complex has been given 21 different names in the literature. Since all particles were shown to be identical the name 'proteasome' (which is now generally accepted) was proposed first, referring to its proteolytic and particulate nature [Arrigo et al., *Nature* 331: 192–194 (1988); Faulkenburg et al., *Nature* 331: 190–192 (1988); Brown et al., *Nature* 353: 355–357 (1991)].

Overall Characteristics and Properties

The 20S proteasome is the major cytosolic protease in eukaryotic cells and is the proteolytic component of the ubiquitin-dependent degradative pathway. Proteasomes are also found in some, but not all, archaebacteria and eubacteria, and in eukaryotes. True proteasomes are composed of 28 subunits, 14 each of two different classes—non-catalytic alpha (α) and catalytically-active beta (β) subunits. The subunits are arranged in rings of seven subunits, all of a single type. The 20S proteasome is a stack of four rings, two inner beta rings flanked by the alpha rings. The junction between the beta rings produces a remarkable structural feature of proteasomes—an interior aqueous cavity large enough to accommodate about 70 kDa of protein and accessible only through narrow axial channels in the rings. The catalytic sites are located on the beta subunits within the aqueous cavity. Isolation of the catalytic sites in this way, and the limited access via narrow channels, serves to compartmentalize proteolysis, allowing degradation of only those proteins that can be actively translocated into the interior of the proteasome.

Structure and Subunit Components

The 20S proteasome has a cylindrical or barrel-like structure, typically 14.8 nm in length and 11.3 nm in diameter. It is composed of 28 subunits and arranged in four stacked rings, resulting in a molecular mass of about 700 kDa. This overall structural architecture is conserved from bacteria to man.

Figure 9:
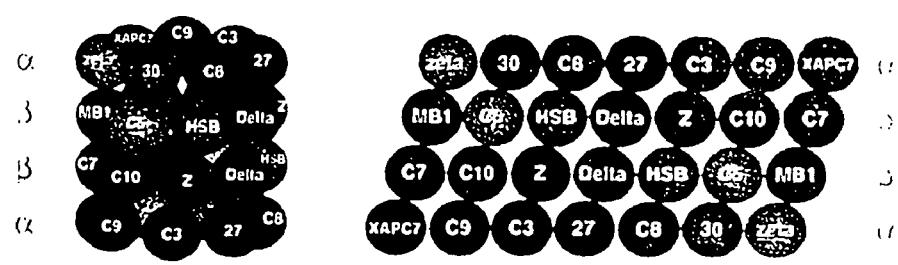
FIG. 9 presents Table 3 illustrating a schematic representation of the human 20S proteasome.

In eukaryotes, including humans, 14 different subunits, ranging from 21 kDa to 32 kDa, are present in the complex. Based on the sequence homology with the *T. acidophilum* α- or β-subunit, the eukaryotic subunits are divided into α-type and β-type, respectively [Zwicki et al., *Biochemistry* 31: 964–972 (1992); Heinemeyer et al., *Biochemistry* 33: 12229–12237 (1994); Coux et al., *Mol. Gen. Genet.* 245: 769–780 (1994)]. Table 2 shows some characteristics and alternative names of the subunits of the human and yeast 20S proteasome using the older and the new nomenclature proposed by Groll and coworkers [Groll et al., *Nature* 386: 463–471 (1997)]. Immuno-electron microscopy (EM) studies also revealed that the eukaryotic α-type subunits reside in the outer rings and the β-type subunits in the inner rings. Furthermore, these studies indicated that in the eukaryotic 20S proteasome seven different subunit constitute a ring, each subunit located at a defined position [Kopp et al., *J. Mol. Biol.* 229: 14–19 (1993); Kopp et al., *J. Mol. Biol.* 248: 264–272 (1995); Schauer et al., *J. Struct. Biol.* 111: 135–147 (1993); Kopp et al., *Proc Natl Acad Sci USA* 94: 2939–2944 (1997)]. Therefore, the eukaryotic proteasome assembles as an $\alpha_{1-7}\beta_{1-7}\beta_{1-7}\alpha_{1-7}$ particle. The typical human structure and assembly is illustrated by Table 3 presented by FIG. 9 hereinafter.

TABLE 2

Nomenclature and molecular masses of proteasomal subunits

| Systematic name | Human gene | Yeast gene | Molecular mass of human subunit (kDa) |
|---|---|---|---|
| α1 | HsPROS27 HsIota | C7 PRS2 | 27.4 |
| α2 | HsC3 | Y7 | 25.9 |
| α3 | HsC9 | Y13 | 29.5 |
| α4 | XAPC7 HsC6 | PRE6 | 27.9 |
| α5 | HsZeta | PUP2 | 26.4 |
| α6 | HsPROS30 HsC2 | PRE5 | 30.2 |
| α7 | HsC8 | C1 PRS1 | 28.4 |
| β1 | HsDelta Y | PRE3 | 25.3 (21.9) |
| β1i | LMP2 | | 23.2 (20.9) |
| β2 | Z | PUP1 | 30.0 (24.5) |
| β2i | MECL1 | | 28.9 (23.8) |
| β3 | HsC10-11 | PUP3 | 22.9 |
| β4 | HsC7-1 | PRE1 C11 | 22.8 |
| β5 | MB1 X | PRE2 | nd (22.4) |
| β5i | LMP7 | | 30.4 (21.2) |
| β6 | HsC5 | C5 PRS3 | 26.5 (23.3) |
| β7 | HsBPROS26 HsN3 | Pre4 | 29.2 (24.4) |

*Reproduced from Gerards et al., CMLS 54: 253–262 (1998)

Proteolytic Activity

The first report on the multicatalytic properties of the proteasome stems from 1983, when three different proteolytic activities were distinguished: 'trypsin-like', 'chymotrypsin-like' and 'peptidylglutamyl-peptide hydrolase' activity [Wilk, S. and M. Orlowski, *J. Neurochem.* 40: 842–849 (1983)]. These three proteasomal activities refer to peptide bond cleavage at the carboxyl side of basic, hydrophobic and acidic amino acid residues, respectively. They were identified using short synthetic peptide substrates and are believed to be catalyzed at independent sites—in part because the different proteolytic activities respond differentially to various activators and inhibitors. With similar approaches, at least two additional proteolytic activities have been recently described [Orlowski et al., *Biochemistry* 32: 1563–1572 (1993); Orlowski, M., *Biochemistry* 29: 10289–10297 (1990); Rivett, A. J., *Biochem. J.* 291: 1–10 (1993)].

The Progressive Degradation of Protein Substrates

Recent studies have also revealed a fundamental new property of the proteasome that clearly distinguishes it from conventional proteases: i.e., this particle degrades a protein substrate all the way to small peptides, before attacking another protein substrate [Akopian et al., *J. Biol. Chem.* 272: 1791–1798 (1997)]. Because the proteasome's multiple active sites are located in its central chamber and because diffusion of a peptide substrate into this compartment must be a slow process, these particles function in a highly processive fashion; i.e., they have mechanisms of action to bind tightly protein substrates and to make multiple cleavages in the polypeptide before releasing the peptide products. Moreover, the ratio of new peptides generated to the number of substrate molecules consumed is constant during the reaction. In other words, as peptides accumulated, they were not hydrolyzed further, even during prolonged incubations, where up to half of the substrate molecules were consumed. Equally important, the disappearance of these substrate molecules coincided exactly with the appearance of small peptide products [Goldberg et al., *Biol. Chem.* 378: 131–140 (1997)]. These observations, together with the finding that the pattern of the products is independent of time, established that processive degradation is a general feature of the 20S proteasome [Gerard et al., *CMLS* 54: 253–262 (1998)].

The contribution of each individual active center and proteolytic activity to the degradation of longer peptides and complete proteins is presently unknown. Nevertheless, proteasomes are able to cleave behind most amino acids in a protein. Thus, the 20S proteasome is in fact a nonspecific endopeptidase. In addition, however, the generated (degraded) peptides fall into a rather narrow size range of 6 to 10 amino acids in length, demonstrating the existence of a kind of 'molecular ruler'. The average length of the degradation products is typically 7 to 8 amino acids; this finding is in agreement with the distance between the active sites in the proteasome. Similar nonspecific endopeptidase activity and size distribution of degration products from whole proteins was observed for proteasomes generally and by proteasomes of human origin in particular.

Other features of the 20S proteasome degradation are also unique. While unfolded peptides are usually digested, most native proteins are resistant to proteolytic degradation by the 20S proteasome in vitro. However, denaturation of the substrate protein by oxidation or reduction of disulphide bridges can render it accessible to degradation by proteasomes. Also, small gold particles with a diameter of 2 nm containing unfolded substrate cannot enter the proteasome. These characteristics show that a relatively narrow opening controls access to the inner proteolytic compartment of the proteasome.

III. The PR-39 Oligopeptide Collective

Native PR-39 peptide is a substance belonging to the cathelin family of proteins; the mature peptide is 39 amino acids in length in the naturally occurring state; and the peptide is able to exert a variety of activities and cause different cellular outcomes. Although first identified as a membrane permeating antibacterial peptide found in the intestine of pigs [Agerberth et al., *Eur. J. Biochem.* 202: 849–854 (1991)], this peptide was subsequently isolated from wounds where it could simultaneously reduce infection and influence the action of growth factors, matrix components, and other cellular effectors involved in wound repair [Gallo et al., *Proc. Natl. Acad. Sci. USA* 91: 11035–11039 (1994); Gallo et al., *J. Invest. Dermatel.* 104: 555 (1995)]. The structure and membrane interactions of native PR-39 peptide have also been elucidated [Cariaux et al., *Eur. J. Biochem.* 224: 1019–1027 (1994)] and the complete amino acid sequences of native PR-39 peptide and its various substituted forms have been reported [PCT Publication No. WO 92/22578 published 23 Dec. 1992].

More recently, the native PR-39 peptide was shown to possess a syndecan-inducing activity in furtherance of its wound healing capabilities; and while renamed a "syndu-cin", was shown to induce cellular production of two specific proteoglycans, syndecan-1 and syndecan-4, within living mesenchymal cells [U.S. Pat. No. 5,654,273]. Overall, native PR-39 peptide has been shown to play a role in several inflammatory events including wound healing and myocardial infarction [Gallo et al., *Proc Natl. Acad. Sci. USA* 21: 11035–11039 (1994); Li et al., *Circ. Res.* 81: 785–796 (1997)]; and the native peptide has been shown to be taken up rapidly by a number of different cell types including meschymal cells and endothelial cells [Chan, Y. R. and R. L. Gallo, *J. Biol. Chem.* 273: 28978–28985 (1998)].

The PR-39 Peptide Grouping

Native PR-39 peptide is composed of the 39 amino acid sequence shown below (and also by Table 4).

PR-39: Arg-Arg-Arg-Pro-Arg-Pro-Pro-Tyr-Leu-Pro-Arg-Pro-Arg-Pro-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro (SEQ ID NO:1)

As conventionally known and reported [see for example, U.S. Pat. No. 5,654,273], the specific peptide can be substituted using conservative substitutions of amino acids having the same or functionally equivalent charge and structure, except for the required amino acid sequence "Arg-Arg-Arg" at the N-terminus and the intermediate amino acid sequences "Pro-Pro-X-X-Pro-Pro-X-X-Pro" (SEQ ID NO:2) and "Pro-Pro-X-X-X-Pro-Pro-X-X-Pro" (SEQ ID NO:3) where X can be substituted freely using any amino acid. Thus, all of the preferred substituted amino acid sequences are of about the same size and each differ from the native PR-39 peptide sequence only by substitutions in the intermediate portions of the structure.

The PR-39 Derived Oligopeptide Family

In addition to the conventionally known native PR-39 peptide amino acid residue sequence and its readily recognizable substituted forms as described above, an entirely novel and unforeseen family of PR-39 derived oligopeptide structures is provided by the present invention for use. This previously unknown family of PR-39 derived oligopeptides is constituted of members which individually will cause a selective inhibition of proteasome-mediated degradation of peptides in-situ after introduction intracellularly to a viable cell.

Each member of this PR-39 derived oligopeptide family presents characteristics and properties which are commonly shared among the entire membership. These include the following:

(i) each peptide sequence is less than 39 amino acid residues in length in every embodiment, and preferably is less than 20 residues in size in the best mode;

(ii) each short-length peptide sequence is at least partially homologous (or analogous) with the N-terminal amino acid residues of the native PR-39 peptide, and preferably is completely identical or markedly similar to the N-terminal end residues of the native PR-39 peptide;

(iii) each short-length peptide is able to interact in-situ with at least the α7 subunit of such proteasomes as are present within the cytoplasm of the cell; and (iv) each short-length peptide sequence is able to alter markedly the proteolytic activity of proteasomes with an interacting α7 subunit such that a selective increased expression of specific proteins (such as IκBα and HIF-1α) occurs in-situ.

Merely as illustrative examples and preferred embodiments of the broad membership constituting this PR-39 derived oligopeptide family, the members comprising 15, 11 and 8 amino acid residues respectively in length are presented below as the PR15, PR11, and PR8 entities respectively. For comparison purposes only, the complete amino acid sequence of the native PR-39 peptide is presented as well.

```
PR-39:  1   2   3   4   5   6   7   8   9   10  11  12      (SEQ ID NO:1)
        Arg-Arg-Arg-Pro-Arg-Pro-Pro-Tyr-Leu-Pro-Arg-Pro- 13  14  15  16  17  18  19  20  21  22  23  24
        Arg-Pro-Pro-Pro-Phe-Phe-Pro-Pro-Arg-Leu-Pro-Pro- 25  26  27  28  29  30  31  32  33  34  35  36
        Arg-Ile-Pro-Pro-Gly-Phe-Pro-Pro-Arg-Phe-Pro-Pro- 37  38  39
        Arg-Phe-Pro

PR-15:  1   2   3   4   5   6   7   8   9   10  11  12      (SEQ ID NO:4)
        Arg-Arg-Arg-Pro-Arg-Pro-Pro-Tyr-Leu-Pro-Arg-Pro- 13  14  15
        Arg-Pro-Pro

PR-11:  1   2   3   4   5   6   7   8   9   10  11          (SEQ ID NO:5)
        Arg-Arg-Arg-Pro-Arg-Pro-Pro-Tyr-Leu-Pro-Arg

PR-8:   1   2   3   4   5   6   7   8                       (SEQ ID NO: 6)
        Arg-Arg-Arg-Pro-Arg-Pro-Pro-Tyr
```

The PR-39 Oligopeptide Collective

Terminology and nomenclature often pose problems for the reader as to what precisely is meant. Accordingly, for definitional purposes, avoidance of ambiguities, and clarity of understanding, the following terms and titles will be employed herein. The term "PR-39 peptides grouping" includes by definition the native PR-39 structure and all substituted forms conventionally known of the naturally occurring 39 length amino acid sequence. In distinction, the term "PR-39 derived oligopeptide family" and its members includes by definition all the previously unknown shorter-length homologs and analogs of the native PR-39 structure as described above. Finally, the umbrella term and category title "PR-39 oligopeptide collective" includes by definition both the 'PR-39 peptide grouping' as well as the 'PR-39 derived oligopeptide family' members, and identifies any and all individual structures falling into either of the two subset categories.

Synthesis

The PR-39 peptide can be synthesized using standard amino acid synthetic techniques. An example is the conventionally used solid phase synthesis [Merrifield, J., J. Am. Chem. Soc. 85: 2149 (1964)] described in U.S. Pat. No. 4,244,946, wherein a protected alpha-amino acid is coupled to a suitable resin, to initiate synthesis of a peptide starting from the C-terminus of the peptide. Other methods of peptide synthesis are described in U.S. Pat. Nos. 4,305,872 and 4,316,891, the teachings of which are incorporated herein. These methods can be used to synthesize peptides having identity with the native PR-39 peptide amino acid sequence described herein, or to construct desired substitutions or additions of specific amino acids, which can be screened for content and evaluated for activity. PR-39 can also be commercially obtained from Magainin, Inc. (Plymouth Meeting, Pa.).

Pharmaceutical Formats

After synthesis or purchase, the PR-39 peptides (as a family of homologs and analogs with substituted amino acid residues) can be introduced as a peptide-containing preparation in a pharmaceutically acceptable format.

The PR-39 can be administered and introduced in-vivo systemically, topically, or locally. The peptide can be administered as the peptide or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines).

PR-39 peptide and any of the PR-39 derived oligopeptide family members may also be conjugated to sugars, lipids, other polypeptides, nucleic acids and PNA; and function in-situ as a conjugate or be released locally after reaching a targeted tissue or organ. The PR-39 family of peptides may also be linked to targeting compounds for attachment in-situ to a specific cell type, tissue or organ.

IV. Means For Introduction of PR-39 Peptide and/or its Shorter-Length Derived Homologs DNA Fragments and Expression Vectors A variety of means and methods are conventionally known and presently available to the user or practitioner of the present invention in order to introduce PR-39 peptide (or a derived oligopeptide family member) to living cells and tissues. One desirable means uses a prepared DNA sequence fragment encoding the PR-39 peptide (or a shorter-length homolog) in a suitable vector as the means of introduction to the intended target in-situ. These means for delivery envision and include in-vivo use circumstances; ex-vivo specimens and conditions; and in-vitro cultures. In addition, the present invention intends and expects that the prepared DNA sequence fragment coding for PR-39 peptide (or shorter-length homologs) has been inserted in a suitable expression vector and will be used in a route of administration for delivery to living tissues comprising endothelial cells, and typically vascular endothelial cells which constitute the basal layer of cells within capillaries and blood vessels generally. Clearly, the cell recipients themselves are thus eukarytoic in origin, typically mammalian cells from human and animal sources; and most typically would include the higher orders of mammals such as humans and domesticated mammalian animals kept as pets or sources of food intended for future consumption. Accordingly, the range of animals includes all domesticated varieties involved in nutrition including cattle, sheep, pigs and the like; as well as those animals typically used as pets or raised for commercial purposes including horses, dogs, cats, and other living mammals typically living with and around humans.

Clearly, the expression vectors must be suitable for transfection of endothelial cells in living tissues of mammalian origin and thus be compatible with that type and condition of cells under both in-vivo and/or in-vitro conditions. The expression vectors thus typically include plasmids and viruses as expression vectors.

Also, both the plasmid based vectors and the viral expression vectors constitute conventionally known means and methods of introduction which are conventionally recognized today as "gene therapy" modes of delivery. However, this overall approach is not the only means and method of delivery available for the present invention.

Direct Introduction of Previously Synthesized PR-39 Peptides or a PR-39 Derived Oligopeptide Family Member PR-39 peptide or an oligopeptide family member can be introduced directly as a synthesized compound to living cells and tissues via a range of different delivery means. These include the following.

1. Intracoronary delivery is accomplished using catheter-based deliveries of synthesized PR-39 peptide (or homolog member) suspended in a suitable buffer (such as saline) which can be injected locally (i.e., by injecting into the myocardium through the vessel wall) in the coronary artery using a suitable local delivery catheter such as a 10 mm InfusaSleeve catheter (Local Med, Palo Alto, Calif.) loaded over a 3.0 mm×20 mm angioplasty balloon, delivered over a 0.014 inch angioplasty guidewire. Delivery is typically accomplished by first inflating the angioplasty balloon to 30 psi, and then delivering the protein through the local delivery catheter at 80 psi over 30 seconds (this can be modified to suit the delivery catheter).

2. Intracoronary bolus infusion of PR-39 peptide (or a short-length homolog) synthesized previously can be accomplished by a manual injection of the substance through an Ultrafuse-X dual lumen catheter (SciMed, Minneapolis, Minn.) or another suitable device into proximal orifices of coronary arteries over 10 minutes.

3. Pericardial delivery of synthesized PR-39 peptide (or a shorter-length homolog) is typically accomplished by instillation of the peptide-containing solution into the pericardial sac. The pericardium is accessed via a right atrial puncture, transthoracic puncture or via a direct surgical approach. Once the access is established, the peptide material is infused into the pericardial cavity and the catheter is withdrawn. Alternatively, the delivery is accomplished via the aid of slow-release polymers such as heparin-alginate or ethylene vinyl acetate (EVAc). In both cases, once the PR-39 peptide (or homolog) is integrated into the polymer, the desired amount of PR-39/polymer is inserted under the epicardial fat or secured to the myocardial surface using, for example, sutures. In addition, the PR-39/polymer can be positioned along the adventitial surface of coronary vessels.

4. Intramyocardial delivery of synthesized PR-39 peptide (or a shorter-length homolog) can be accomplished either under direct vision following thoracotomy or using thoracoscope or via a catheter. In either case, the peptide containing solution is injected using a syringe or other suitable device directly into the myocardium. Up to 2 cc of volume can be injected into any given spot and multiple locations (up to 30 injections) can be done in each patient. Catheter-based injections are carried out under fluoroscopic, ultrasound or Biosense NOGA guidance. In all cases after catheter introduction into the left ventricle the desired area of the myocardium is injected using a catheter that allows for controlled local delivery of the material.

Pharmaceutical Carriers of PR-39 Peptides or a PR-39 Derived Oligopeptide Family Member A range of suitable pharmaceutical carriers and vehicles are known conventionally to those skilled in the art. Thus, for parenteral administration, the compound will typically be dissolved or suspended in sterile water or saline.

For enteral administration, the PR-39 peptide or homologous oligopeptide of choice will be typically incorporated into an inert carrier in tablet, liquid, or capsular form. Some suitable carriers are starches and sugars; and often include lubricants, flavorings, binders, and other materials desirable in tablet making procedures.

The PR-39 peptide and oligopeptide family of compounds can also be administered topically by application of a solution, cream, gel, or polymeric material (for example, a Pluronic™, BASF).

As an alternative, the chosen peptide can be administered in liposomes or microspheres (or microparticles), which can be injected for local or systemic delivery. Methods for preparing liposomes and microspheres for administration to a patient are conventionally known to those skilled in the art. For example, U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. See also, G. Gregoriadis, Chapter 14, "Liposomes", *Drug Carriers in Biology and Medicine*, chap. 14, pp. 287–341 (1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted from days to months. See, for example, U.S. Pat. Nos. 4,906,474; 4,925,673; and 3,625,214.

Examplary Introductions and Preferred Routes of Administration

A variety of approaches, routes of administration, and delivery methods have been identified herein and are available for introduction of PR-39 peptide and the derived family of oligopeptides. It is envisioned, however, that a majority of the approaches and routes of administration described herein will be medical applications and specific clinical approaches intended for use with individual human patients having specified medical problems and diagnosed pathologies. It is expected, accordingly, that the reader is familiar generally with the typical clinical human problem, pathology, and medical conditions described herein; and therefore will be able to follow and easily understand the nature of the intervention clinically using the present invention and the intended outcome and result of the clinical treatment—particularly as pertains to the stimulation of angiogenesis under in-vivo treatment conditions. A representative listing of preferred clinical approaches is given by Table 5 below.

TABLE 5

Preferred Routes of Administration

Catheter-based (intracoronary) injections and infusions;
Direct myocardial injection
   (intramyocardial guided);
Direct myocardial injection
   (direct vision-epicardial-open chest or under thorascope guidance);
Local intravascular delivery;
Liposome-based delivery;
Delivery in association with receptor-specific peptides;
Oral delivery;
In instances of peripheral vascular disease:
   intramuscular injection
   intraarterial injection and/or infusion.

V. Experiments and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Introduction

Proteolytic degradation in mammalian cells is known to proceed via two distinct pathways: lysosome-dependent degradation and proteasome-dependent. The proteasome in its pathway plays a key role in proteolysis of intracellular proteins which are marked for degradation by the ubiquitin system. The multienzyme complex involved in these events, the 26S proteasome, consists of a 20S catalytic proteasome "core" and two 19S caps that bind uniquitylated proteins, as has been described in detail previously herein. Proteasome-mediated proteolysis is a principal event quantitatively controlling intracellular levels of a number of different proteins including hypoxia-inducing factor (HIF)-1α, heat shock protein HSP70, protooncogenes c-Fos, c-Jun and c-Mos, NFκB inhibitor IκBα, and various cyclins. In addition, the proteasome also is known to play a critical role in the specific processing and presentation of major histocompatibility complex (MHC) class I-restricted antigens as well as provide partial proteolytic cleavage of p105 NFκB to the active p50 subunit.

The PR-39 peptide, belonging to the cathelin family of proteins, plays an important role in several inflammatory events including wound healing and myocardial infarction. The PR-39 peptide typically is rapidly taken up by a number of different cell types including endothelial cells; and prolonged treatment with PR-39 peptide leads to increased cell growth and angiogenesis. However, the mechanism of action for this peptide activity has yet to be understood or defined. The experiments and data presented below reveal for the first time the nature and detailed intracellular actions exerted by the PR-39 peptide.

Methods and Materials

Yeast Two-Hybrid Screening

Two-hybrid screening was carried out using MATCH-MAKER GAL4 System 2 (Clontech) with exon 4 of the porcine PR-39 gene as a bait to screen the mouse embryo 3T3 cDNA library in yeast CG1945.

Cell Culture Studies

U937 cells (ATCC) grown in RPMI medium 1640 with 10% FBS (Gibco-BRL) and ECV cells were treated with synthetic PR-39, lactacystin (CalBiochem, 426100) or MG6132 (CalBiochem, 474790) at concentration indicated in the presence of 100 mM cyclohexamide 20 mM chloroquine [Merin et al., *J. Biol. Chem.* 273: 6373–6379 (1995)]. After 45 min. of incubation, TNFα (1 ng/ml) was added. After 5 min of 37° C. incubation, the cells were lysed in SDS-PAGE loading buffer. Following SDS-PAGE of the total protein extract, IκB-α and NF-κB p105 p50 expressions were determined by Western blotting with anti-human antibodies (Santa Cruz, sc-203, sc 14G). For studies of HIF-1α and VEGF expression, ECV cells were cultured in a hypoxia chamber (5% $CO_2$/95% $N_2$) at 37° C. for 16 hr. HIF-1α was immunoprecipitated with anti-HIF-1α mAb (OZ12 1:5) in RIPA buffer and Western blotting with anti-HIF-1α mAb (OZ15 1:10) (courtesy of Dr. A. King, DFCI, Boston). VEGF expression was shown by Western blotting of hypoxia treated ECV cell lysate with anti-human VEGF antibody (Santa Cruz, sc-152). For HSP70 expression, U937 was treated for 3 hr, harvest with SDS-PAGE loading buffer, Western blotting with anti-human HSP70 polyclonal antibody (Santa Cruz, sc-1060).

In-Vitro Proteasome Activity Assays

Rabbit muscle 20S proteasome preparation (courtesy of Dr. M. Sherman, BBRI, Boston) was used for all studies. For determination of proteasome activity, 5 µl of 1:10 diluted proteasome preparation was incubated at room temperature in eukaryotic proteasome assay buffer (20 mM Tris-HCl pH 8.0, 0.5 mM EDTA and 0.01% SDS) with 20 µM proteasome substrates (CalBiochem, 539140–3) and PR-39 or other proteasome inhibitor at indicated concentration [Rock et al., *Cell* 78: 761–771 (1994)]. The extent of substrate degradation was monitored continuously by fluorescence spectrophotometry (380 nm excitation, 460 nm emission Hitachi F-2000) for 10 min.

EXPERIMENT 1

This experiment was designed to reveal the ability of PR-39 peptide to affect proteasome function. To test this capability, the effect of PR-39 administration upon α7 subunit processing was empirically determined. The results are illustrated by FIGS. 1A–1D respectively.

Experimentally, a peptide corresponding to the 4th exon porcine PR-39 gene sequence was used to generate a rabbit polyclonal antibody RPE4. Full length porcine cDNA (containing leader sequence) and a sequence corresponding to the 4th exon of porcine PR-39 gene were cloned into eukaryotic expression vector pGRE5-2 (USB). These expression constructs were then used to stably transfect an immortalized human endothelial cell line (ECV304, ATCC). For co-immunoprecipitation, wild type ECV, full length PR-39 (ECV-PR39) and exon 4 PR39 and exon 4 PR39 (ECV-E4) transfected cells were cultured in Medium 199 with 10% fetal bovine serum (FBS) and penicillin/streptomycin. Cells were lysed with RIPA buffer; immunoprecipitated with 10 µg affinity purified rabbit anti-PR39 antibody; and following Protein A-Sepharose purification and SDS-PAGE, subjected to immunoblotting with 1:1000 mouse anti-HC8 mAb (Affiniti Research Products Limited UK, PW8110).

FIGS. 1A–1D show the interactions of PR-39 peptide and the α7 subunit of proteasomes. FIG. 1A recites the cDNA sequence of cloned mouse α7 subunit (top; GeneBank accession number AF055983) and corresponding human HC8 subunit of 20S proteasome. FIG. 1B shows the sequence alignment of C-terminal tails mouse α subunits of 20S proteasome. FIG. 1C shows a deletion analysis of α7-PR39 binding. Deletion mutants of the mouse α7 subunit were cloned into an yeast-two hybrid vector and the extent of growth of lacZ$^+$ colonies on selective medium following co-transformation with PR-39 construct in the yeast CG1945 was determined. It is noted that only full length α7 construct was able to bind to PR-39. Finally, FIG. 1D shows the co-immunoprecipitation of PR-39 and α7 subunit in ECV cells.

It will be noted also that FIG. 1 represents the evidence of four clones growing on selective media and demonstrating lacZ staining. All four clones encoded overlapping identical cDNA sequences highly homologous to the human sequence of α7 (HC8) subunit of proteasome (FIG. 1A). Similar to all α subunits of the 20S proteasome, the cloned mouse protein possesses a highly conserved N-terminal region; in addition it demonstrated the presence of 16 amino acid long C-terminal sequence found in some but not all α subunits (FIG. 1B). Deletion analysis showed that the presence of both C-terminal as well as N-terminal amino acids sequences was required for PR-39 binding (FIG. 1C). In order to confirm the PR39-α7 subunit interaction in-vivo, anti-PR39 antibody was used to immunoprecipitate PR39 protein from ECV-PR39, ECV-E4 and mock-transfected ECV cells. Western blotting of the immunoprecipitate from ECV-PR39 and ECV-E4 but not wild type ECV cells with anti-α7 subunit antibody demonstrated the presence of a 29 kDa band corresponding to the known size of α7 subunit protein (FIG. 1D). The evidence therefore reveals that PR39 peptide interacts with α7 subunit of proteasome in ECV cells.

EXPERIMENT 2

To test the ability of PR-39 peptide to affect proteasome function in-vivo, the effect of PR-39 peptide administration on IκBα processing was assessed. The results are illustrated by FIGS. 2A–2D respectively.

Figure 2A:
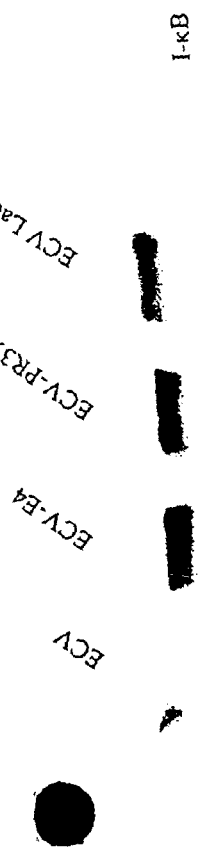

FIG. 2A shows a Western analysis of IκBα expression in ECV cells. The results show that pretreatment of cultured ECV cells with lactacystin (10 µM, 4th lane) or stable expression of full length (ECV-PR39) or PR39 exon 4 (ECV-E4) constructs inhibited TNF-α-induced degradation of IκB.

Thus, tumor necrosis factor (TNF)-α induces rapid degradation of IκBα-a function that is blocked by the proteasome inhibitor lactacystin. However, Western analysis of IκBα levels after TNF-α treatment demonstrated comparable levels of IκBα expression in both ECV-PR39 and ECV-E4 cells to that seen in ECV cells pre-treated with lactacystin.

Figure 2D:
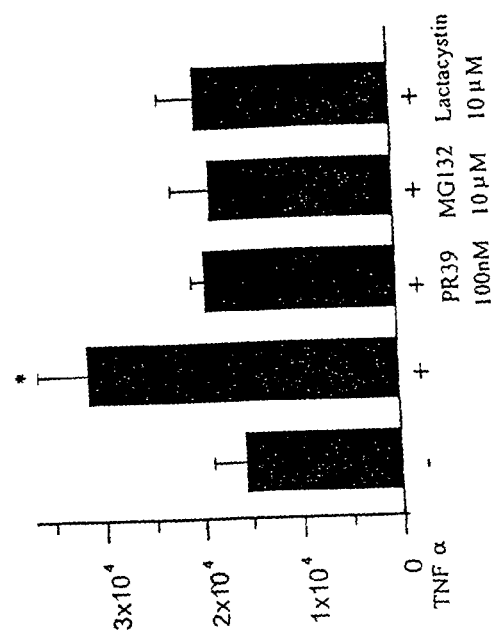
Figure 2B:
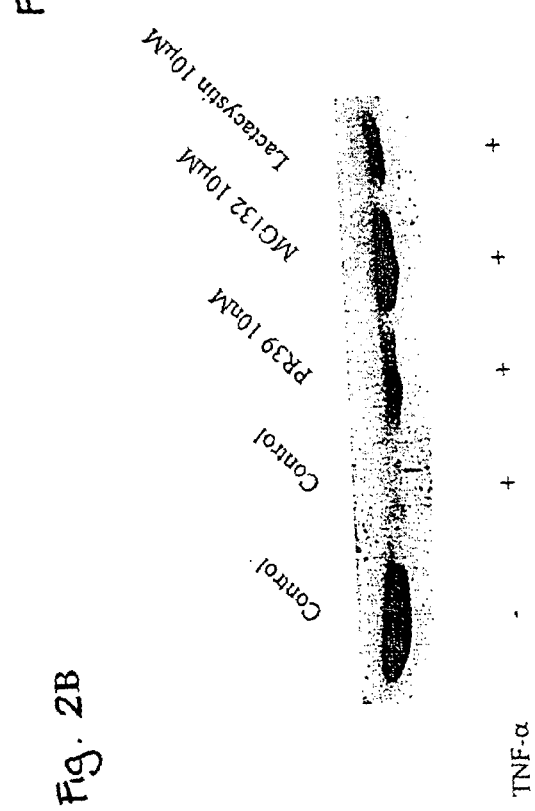

FIG. 2B shows the effect of PR39, MG132 and lactacystin pretreatment on IκBα expression in U937 cells following TNF-α treatment. Note similar extent of inhibition of IκBα degradation by TNF-α following pretreatment with PR39, MG132 or lactacystin. Thus, it is clear that pretreatment of U937 cells with PR39 blocked TNF-α induced IκBα degradation in a manner that was similar to the degree of inhibition seen with MG132 and lactacystin.

FIG. 2C demonstrates the reversibility of PR39 inhibition of proteasome activity. U937 cells were pretreated with PR39, MG132 or lactacystin for 45 min. After that time, the cells were extensively washed with fresh medium. 45 min later TNF-α (1 ng/ml) was added to the medium and the extent of IκBα degradation was determined 10 min later by Western blotting. Note preservation of IκBα in lactacystin but not PR39-treated cells. Thus, unlike lactacystin but similar to MG132, PR-39 peptide mediated inhibition of IκBα degradation was rapidly reversible.

Finally, to show that PR-39 inhibition of IκBα degradation affected NFκB-dependent transcription, ECV cells were transiently transfected with a NFκB-Luc reporter construct containing a tandem of four NFκB binding sites in front of luciferase cDNA. The results of FIG. 2D show that stimulation with TNF-α induced a significant increase in luciferase activity that was completely inhibited by pretreatment with PR39.

Accordingly, the true functional significance of PR39-mediated inhibition of IκBα degradation in ECV cells transiently transfected with pNFκB-Luc reporter vector (Clontech) is clearly shown by FIG. 2D. Pre-treatment with PR39 completely inhibited TNF-α-induced increase in luciferase activity. *$p<0.01$ vs. control (Luc activity in the absence of TNF-α).

EXPERIMENT 3

To demonstrate directly the ability of PR-39 peptide to inhibit proteasome-mediated protein degradation, preparations of eukaryotic 20S proteasomes were tested for their ability to induce proteolysis of various synthetic peptides in-vitro. The results are graphically illustrated by FIGS. 3A–3D respectively.

For determination of proteasome activity, 5 μl of 1:10 diluted rabbit muscle 20S proteasome preparation (courtesy of Dr. M. Sherman, BBRI, Boston) was incubated at room temperature in an assay buffer (20 mM Tris-HCl pH 8.0, 0.5 mM EDTA and 0.01% SDS) with 20 μM of four different proteasome substrates (CalBiochem, 539140-3) and PR39 or other proteasome inhibitor at indicated concentration. The extent of substrate degradation was monitored continuously by fluorescence spectrophotometry (380 nm excitation, 460 nm emission Hitachi F-2000) for 10 min.

FIGS. 3A–3D reveal that the PR-39 peptide inhibited, in a dose-dependent manner, degradation of all 4 peptides tested. PR-39 peptide was as potent as lactacystin or MG132 in inhibiting degradation in three of the four peptides tested and was considerably more potent in inhibiting degradation of the Z-Leu-Leu-Glu-AMC peptide.

EXPERIMENT 4

To test the effect of PR39 treatment on cellular levels of other proteasome-dependent proteins, the in-vivo expression of p105 and p50 NFκB, HSP70 and HIF-1α within transfected and wild type ECV cells was determined. The results are illustrated by FIGS. 4A–4C respectively.

Figure 4A:
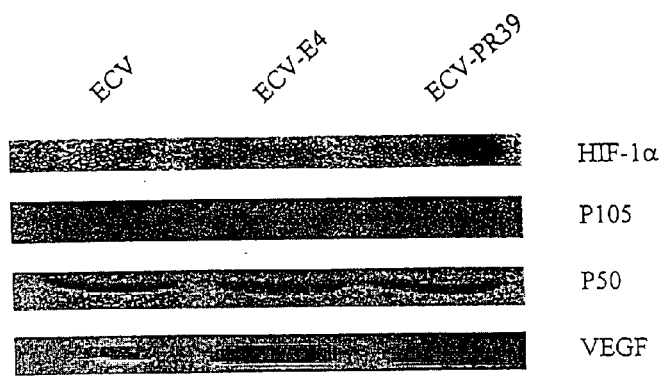
FIGS. 4A–4C are presentations of empirical data showing the in-vivo effects of PR-39 peptide expression.
Figure 4B:
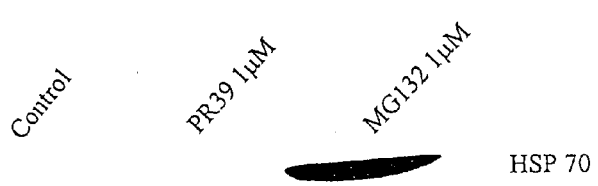
Figure 4C:
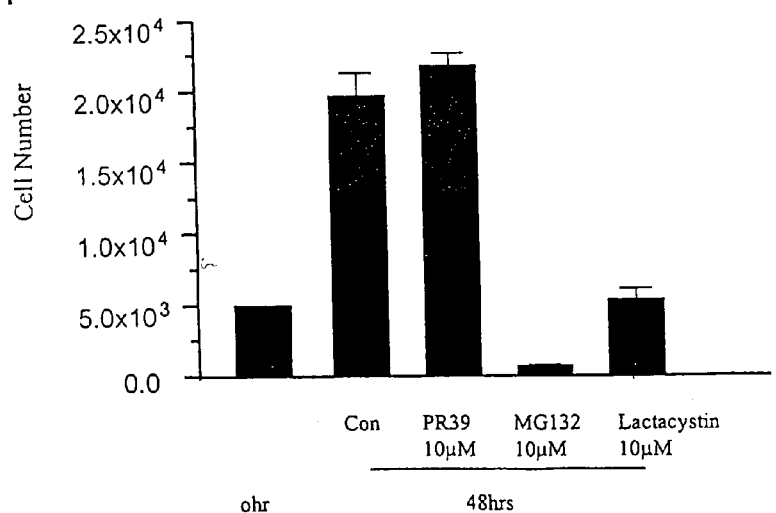

FIG. 4A shows the results of a Western blot analysis of HIF-1α, p50 and p105 NFκB expression in wild type ECV cells and ECV-E4 and ECV-PR39 clones. It is noted that an increase in HIF-1α expression occurs (but not p105 or p50 NFκB expression) in ECV-E4 and ECV-PR 39 clones. Thus, while there was a significant increase in expression of HIF-1α and IκB in PR39 transfected or treated compared to wild type cells, there was no significant change in expression of either HSP70 or NFκB-demonstrating that effects of PR39-proteasome interaction are selective.

Since increased expression of HIF-1α is known to result in increased transcription of a number of angiogenesis-related molecules including VEGF, Northern analysis of VEGF mRNA levels in wild type and PR39 transfected ECV cells was performed. The results are shown by FIG. 4B. As expected, there was a significant increase in expression of both of these genes in ECV-PR39 and ECV-E4 cells compared to ECV controls.

Finally, exposure to proteasome inhibitor lactacystin is known to induce rapid cell death. To test the effect of PR39 on cell survival, growth rates of ECV cells treated with PR39 peptide were assessed. The results are shown by FIG. 4C. 50,000 ECV cells were cultured in 10% FBS-M199 in the absence (control) or presence of 10 μM of PR39, lactacystin or MG132. Note that while exposure to PR39 did not affect cell growth, exposure to lactacystin or MG132 substantially inhibited cell growth. Thus, following 3 days of PR39 exposure, treated cells demonstrated normal growth compared to controls while those cells exposed to lactacystin demonstrated markedly reduced survival.

EXPERIMENT 5

To demonstrate the stimulation of angiogenesis directly in living cells and tissues via the introduction of PR-39 peptide, a mice matrigel assay system was employed. Growth factor-depleted Matrigel pellets containing 5 μg of PR39, 50 ng of FGF2 or saline (control) were inserted intraperitoneally into C57BL/6 mice. Ten days later the pellets were removed, sectioned and stained with anti-CD31 antibody. The number of vessels was determined in multiple sections using a digital camera and Optimas 5.0 software. The results are shown by FIGS. 5A–5C and FIG. 6 respectively.

Figure 5A:
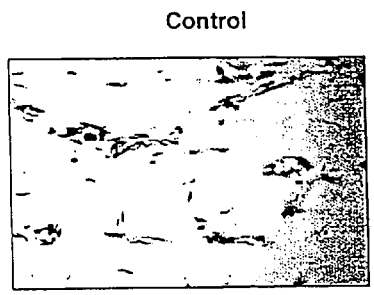
FIGS. 5A–5C are photographs of representative sections showing differences in vascularity among control, PR-39 peptide and FGF2 impregnated Matrigel pellets.
Figure 5C:
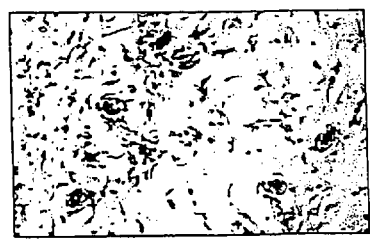
Figure 5B:
Figure 6:
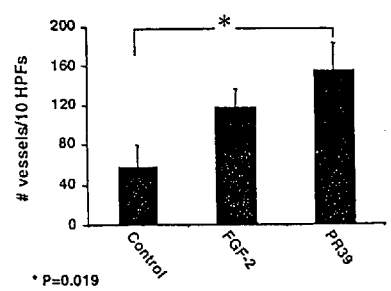
FIG. 6 is a graph providing a quantitative analysis of vascularity for the representative sections of FIG. 5.

FIGS. 5A–5C are representative sections from control, PR39 and FGF2 impregnated Matrigel pellets and FIG. 6 provides a quantitative analysis of vascularity. Clearly, the results of the representative sections and the graphic quantitative evaluations demonstrate that insertion of growth-factor depleted Matrigel pellet containing PR-39 peptide induced intense vessel growth that exceeded that seen with implantation of pellets containing 50 ng/ml of bFGF.

EXPERIMENT 6

To demonstrate the efficiency of shorter-length peptides which collectively are members of the PR-39 derived oligopeptide family in stimulating angiogenesis in-vivo, a novel peptide, PR11, composed of the first 11 amino acid residues [N-terminal end] of the native PR-39 sequence was purposely synthesized. The amino acid sequence of PR11 is as follows:

```
1   2   3   4   5   6   7   8   9   10  11      (SEQ ID NO:5).
Arg-Arg-Arg-Pro-Arg-Pro-Pro-Tyr-Leu-Pro-Arg
```

To introduce the short-length PR11 peptide in-vivo, a mouse Matrigel assay system was utilized. In sum, either 5 µg/ml of PR11 peptide or 5 µg/ml of native PR-39 peptide were individually placed into a growth factor-depleted Matrigel pellet; and then each prepared Matrigel pellet was inserted into the peritoneal cavity of a mouse. After 14 days intraperitoneal placement, each pellet was removed from its living host; and each pellet was examined for evidence of new vascularity. The results are graphically presented by FIG. 7. Note that the bar graph of FIG. 7 shows the number of blood vessels [mean±SD] per 10 high power fields (HPF).

Figure 7:
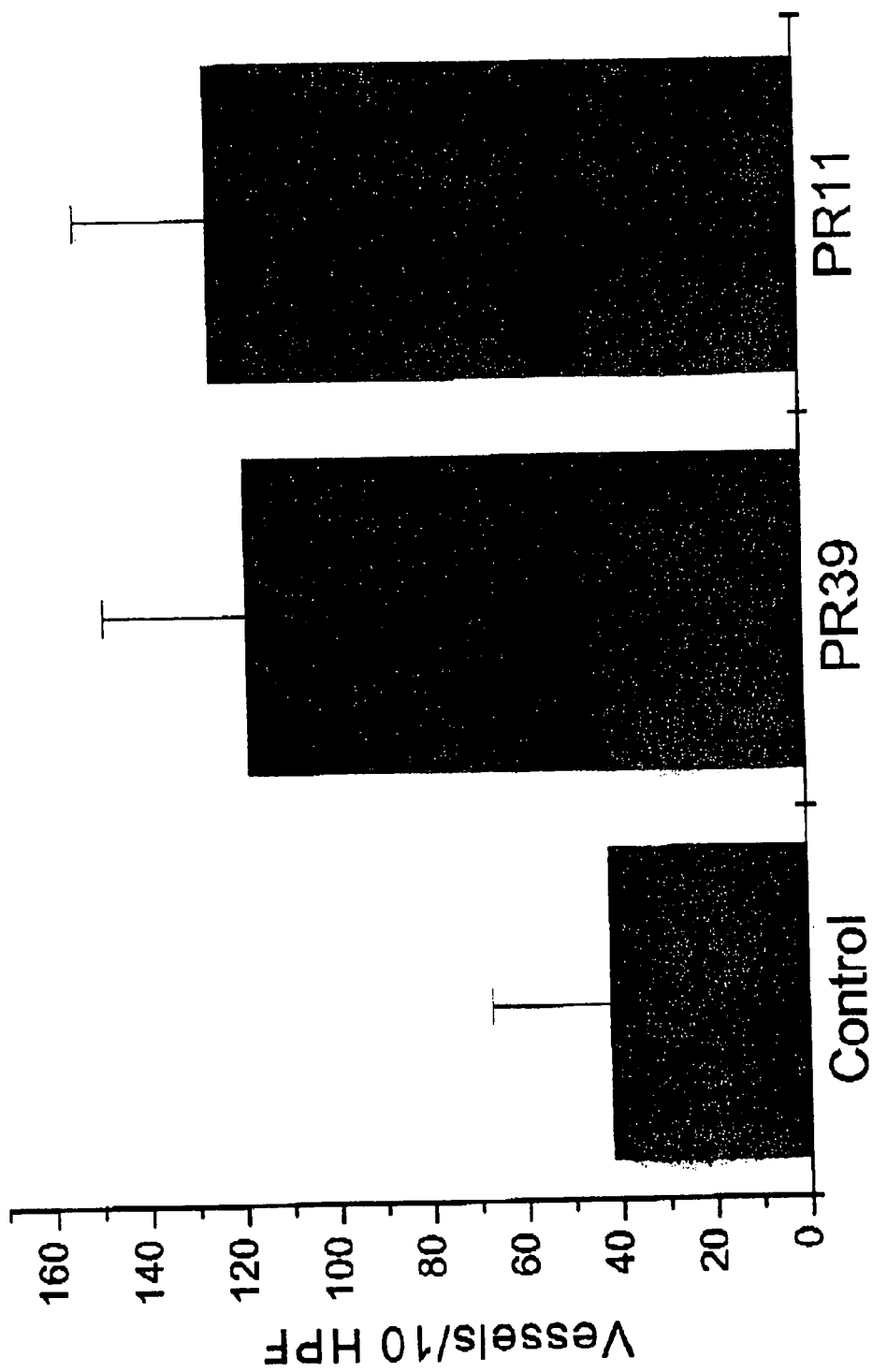
FIG. 7 is a graph showing the induction of angiogenesis in-vivo using PR-39 peptide and short-length PR11 peptide impregnated Matrigel pellets.

As evidenced by FIG. 7, the analysis of Matrigel pellet vascularity after 14 days incubation in-vivo demonstrated significant induction of angiogenesis in both the PR11 and the native PR-39 pellets. The control Matrigel pellets, however, showed no evidence of angiogenesis as such. Clearly therefore, the short-length PR11 peptide is fully efficacious and effective in stimulating angiogenesis in-vivo.

CONCLUSIONS (1) The described experiments and empirical data have demonstrated that PR-39 peptide has the ability to selectively alter activity of 20S proteasome in human endothelial cells by directly interacting with the α7 (HC8) proteasome subunit in a reversible manner with the α7 subunit. This interaction leads to suppression of IκB and HIF-1α degradation while not affecting expression of other proteasome-dependent proteins such as p105 NFκB or HSP70. Unlike other proteasome inhibitors, treatment with PR39 is not associated with any cellular cytotoxicity. Thus, PR39 and its related peptides provide a unique and unforeseen means of regulating cellular function and stimulating angiogenesis.

(2) Several observations also set PR39 apart from the conventionally known proteasome inhibitors. First, PR39-mediated inhibition of IκBα degradation is demonstrably reversible, unlike that of lactacystin. Second, long-term exposure of several cell types to PR39 did not result in any cytotoxicity, in contrast to the rapid cell death typically observed following cell treatment with lactacystin or MG132. This observation shows that PR39 peptide differentially affects processing of various and different intracellular proteins. Also supporting this view is the observation that while increasing HIF-1α expression, PR39 administration had no meaningful effect on the expression of either NFκB or HSP70. Third, PR-39 peptide modulation of proteasome activity plays a functional role since the observed increased expression of HIF-1α was directly associated with an increased expression of its target genes, VEGF and flt-1.

The present invention is not to be limited in form nor restricted in scope except by the claims appended hereto.

SEQUENCE LISTING

```
<160> NUMBER OF SEQ ID NOS: 12

<210> SEQ ID NO 1
<211> LENGTH: 39
<212> TYPE: PRT
<213> ORGANISM: Artificial Sequence
<220> FEATURE:
<223> OTHER INFORMATION: Synthetic peptide

<400> SEQUENCE: 1

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 2
<211> LENGTH: 9
<212> TYPE: PRT
<213> ORGANISM: Artificial Sequence
<220> FEATURE:
<223> OTHER INFORMATION: Synthetic consensus peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

```
<400> SEQUENCE: 2

Pro Pro Xaa Xaa Pro Pro Xaa Xaa Pro
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic consensus sequence
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 3

Pro Pro Xaa Xaa Xaa Pro Pro Xaa Xaa Pro
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Arg Arg Arg Pro Arg Pro Pro Tyr Leu Pro Arg Pro Arg Pro Pro
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Arg Arg Arg Pro Arg Pro Pro Tyr Leu Pro Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Arg Arg Arg Pro Arg Pro Pro Tyr
1               5

<210> SEQ ID NO 7
<211> LENGTH: 255
<212> TYPE: PRT
<213> ORGANISM: Mus musculus

<400> SEQUENCE: 7

Met Ser Ser Ile Gly Thr Gly Tyr Asp Leu Ser Ala Ser Thr Phe Ser
1               5                   10                  15

Pro Asp Gly Arg Val Phe Gln Val Glu Tyr Ala Met Lys Ala Val Glu
                20                  25                  30
```

-continued

```
Asn Ser Ser Thr Ala Ile Gly Ile Arg Cys Lys Asp Gly Val Val Phe
         35                  40                  45

Gly Val Glu Lys Leu Val Leu Ser Lys Leu Tyr Glu Gly Ser Asn
 50                  55                  60

Lys Arg Leu Phe Asn Val Asp Arg His Val Gly Met Ala Val Ala Gly
 65                  70                  75                  80

Leu Leu Ala Asp Ala Arg Ser Leu Ala Asp Ile Ala Arg Glu Ala
                 85                  90                  95

Ser Asn Phe Arg Ser Asn Phe Gly Tyr Asn Ile Pro Leu Lys His Leu
                100                 105                 110

Ala Asp Arg Val Ala Met Tyr Val His Ala Tyr Thr Leu Tyr Ser Ala
                115                 120                 125

Val Arg Pro Phe Gly Cys Ser Phe Met Leu Gly Ser Tyr Ser Ala Asn
130                 135                 140

Asp Gly Ala Gln Leu Tyr Met Ile Asp Met Ser Gly Val Ser Tyr Gly
145                 150                 155                 160

Tyr Trp Gly Cys Ala Ile Gly Lys Ala Arg Gln Ala Ala Lys Thr Glu
                165                 170                 175

Ile Glu Lys Leu Gln Met Lys Glu Met Thr Cys Arg Asp Val Val Lys
                180                 185                 190

Glu Val Ala Lys Ile Ile Tyr Ile Val His Asp Glu Val Lys Asp Lys
                195                 200                 205

Ala Phe Glu Leu Glu Leu Ser Trp Val Gly Glu Leu Thr Lys Gly Arg
                210                 215                 220

His Glu Ile Val Pro Lys Asp Ile Arg Glu Glu Ala Glu Lys Tyr Ala
225                 230                 235                 240

Lys Glu Ser Leu Lys Glu Glu Asp Glu Ser Asp Asp Asn Met
                245                 250                 255
```

```
<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Ala Glu Arg Asp
1

<210> SEQ ID NO 9
<211> LENGTH: 24
<212> TYPE: PRT
<213> ORGANISM: Artificial Sequence
<220> FEATURE:
<223> OTHER INFORMATION: Synthetic peptide

<400> SEQUENCE: 9

Lys Lys His Glu Glu Glu Ala Lys Ala Glu Arg Glu Lys Lys Glu
1               5                   10                  15

Lys Glu Gln Lys Glu Lys Asp Lys
            20

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 10

Glu Lys Glu Lys Glu Glu Asn Glu Lys Lys Gln Lys Lys Ala Ser
1               5                   10                  15

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide

<400> SEQUENCE: 11

Glu Glu Arg Pro Gln Arg Lys Ala Gln Pro Ala Gln Pro Ala Asp Glu
1               5                   10                  15

Pro Ala Glu Lys Ala Asp Glu Pro Met Glu His
            20                  25

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Ala Lys Glu Ser Leu Lys Glu Glu Asp Glu Ser Asp Asp Asp Asn Met
1               5                   10                  15
```

What we claim is:

1. An isolated PR-39 derived oligopeptide consisting of the amino acid sequence Arg-Arg-Arg-Pro-Arg-Pro-Pro-Tyr (SEQ ID NO:6) or Arg-Arg-Arg-Pro-Arg-Pro-Pro-Tyr-Leu-Pro-Arg (SEQ ID NO:5).

* * * * *